(12) United States Patent
Walston et al.

(10) Patent No.: US 10,371,611 B2
(45) Date of Patent: Aug. 6, 2019

(54) MATERIAL TESTING SYSTEM AND METHOD OF USE

(71) Applicants: Rolls-Royce Corporation, Indianapolis, IN (US); Rolls-Royce North American Technologies, Inc., Indianapolis, IN (US)

(72) Inventors: Jeffrey A. Walston, Indianapolis, IN (US); David J. Thomas, Brownsburg, IN (US); Ted J. Freeman, Danville, IN (US)

(73) Assignees: Rolls-Royce North American Technologies Inc., Indianapolis, IN (US); Rolls-Royce Corporation, Indianapolis, IN (US)

( * ) Notice: Subject to any disclaimer, the term of this patent is extended or adjusted under 35 U.S.C. 154(b) by 325 days.

(21) Appl. No.: 15/404,418

(22) Filed: Jan. 12, 2017

(65) Prior Publication Data

US 2018/0195940 A1      Jul. 12, 2018

(51) Int. Cl.
| | |
|---|---|
| *G01N 3/08* | (2006.01) |
| *G01N 33/38* | (2006.01) |
| *G01N 3/02* | (2006.01) |
| *G01N 3/40* | (2006.01) |
| *G01M 5/00* | (2006.01) |
| *G01N 33/00* | (2006.01) |

(52) U.S. Cl.
CPC .............. *G01N 3/08* (2013.01); *G01M 5/005* (2013.01); *G01M 5/0075* (2013.01); *G01N 3/02* (2013.01); *G01N 3/40* (2013.01); *G01N 33/388* (2013.01); *G01N 2033/0003* (2013.01)

(58) Field of Classification Search
CPC .. G01N 3/08; G01N 3/40; G01N 3/02; G01N 33/388; G01N 2033/0003; G01M 1/00
USPC .......................................................... 73/818
See application file for complete search history.

(56) References Cited

U.S. PATENT DOCUMENTS

| | | | | |
|---|---|---|---|---|
| 4,730,498 | A | * | 3/1988 | Blanch ..................... G01N 3/20 73/852 |
| 4,941,359 | A | * | 7/1990 | Quinn ...................... G01N 3/20 73/851 |
| 4,991,446 | A | * | 2/1991 | Bechtel .................... G01N 3/20 73/849 |
| 5,231,882 | A | * | 8/1993 | Bertele .................... G01N 3/32 73/852 |
| 5,383,474 | A | * | 1/1995 | Akhter ................. A61B 5/4504 600/595 |
| 5,905,205 | A | * | 5/1999 | Clay ........................ G01N 3/08 73/819 |
| 6,257,055 | B1 | | 7/2001 | Haeg et al. |
| 6,718,833 | B2 | | 4/2004 | Xie et al. |
| 7,434,670 | B2 | | 10/2008 | Good et al. |
| 7,584,670 | B2 | | 9/2009 | Myers |
| 7,908,929 | B2 | | 3/2011 | Stillinger |
| 8,443,678 | B2 | * | 5/2013 | Nardi ....................... G01N 3/04 73/760 |
| 8,621,935 | B2 | * | 1/2014 | Foltz ........................ G01N 3/04 73/841 |

(Continued)

*Primary Examiner* — Lisa M Caputo
*Assistant Examiner* — Nathaniel T Woodward
(74) *Attorney, Agent, or Firm* — Barnes & Thornburg LLP

(57) ABSTRACT

The present disclosure relates to a material testing system for use in testing material strength of various gas turbine engine components. The material testing system provides a load force onto portions of gas turbine engine components.

18 Claims, 3 Drawing Sheets

(56) References Cited

U.S. PATENT DOCUMENTS

| | | | | |
|---|---|---|---|---|
| 8,863,585 B2* | 10/2014 | Wang | ............. | G01N 3/34 |
| | | | | 73/812 |
| 9,091,617 B2* | 7/2015 | Edelman | ............. | G01N 3/04 |
| 9,097,621 B2* | 8/2015 | Osborne | ............. | G01M 5/005 |
| 9,103,751 B2* | 8/2015 | Negro | ............. | G01N 3/04 |
| 9,354,151 B2* | 5/2016 | Clark | ............. | G01M 5/0075 |
| 2002/0007682 A1* | 1/2002 | Arimond | ............. | G01N 3/08 |
| | | | | 73/818 |
| 2015/0040680 A1* | 2/2015 | Gregg | ............. | G01N 3/24 |
| | | | | 73/842 |

* cited by examiner

MATERIAL TESTING SYSTEM AND METHOD OF USE

FIELD OF THE DISCLOSURE

The present disclosure relates generally to an apparatus for testing materials and more specifically to an apparatus for testing structures comprising ceramic matrix composite and used in gas turbine engines.

BACKGROUND

Various components within a gas turbine engine may be constructed of a ceramic matrix composite (CMC) structure. Testing CMC articles may be used to characterize the material. These components may have many different shapes and sizes such as different heights. Apply test loads in a uniform, repeatable, and predictable manner may be desired when mechanically testing engineering articles.

SUMMARY

The present disclosure may comprise one or more of the following features and combinations thereof.

A material testing system for loading test articles may include a load rod, a rocker arm, and a load distribution system. The load rod may be arranged to move along a load axis to provide a load force to a test article. The rocker arm may be coupled to the load rod for axial movement therewith. The load distribution system may be configured to engage the rocker arm to transfer the load force from the load rod and rocker arm to the test article.

In some embodiments, the rocker arm may include a rocker axis that intersects the load axis, a first end spaced apart from the rocker axis, and a second end spaced apart from the first end to locate the rocker axis between the first end and the second end of the rocker arm. In some embodiments, the rocker arm may be configured to pivot relative to the load rod about the rocker axis.

In some embodiments, the load distribution system may include a first load applicator configured to engage the first end of the rocker arm and a second load applicator configured to engage the second end of the rocker arm. In some embodiments, the first load applicator and the second load applicator may be configured to move axially relative to one another in response to engaging portions of the test article having different heights to cause the rocker arm to pivot about the rocker axis such that the rocker arm applies the force load equally between the first load applicator and the second load applicator.

In some embodiments, the first load applicator includes a first sliding rod and a first shoe. The first sliding rod may extend axially between a first rod end and a second rod end of the first sliding rod. The first rod end of the first sliding rod may be arranged to engage the first end of the rocker arm. The first shoe may be arranged to engage the second end of the first sliding rod. In some embodiments, the first rod end of the first sliding rod may be hemispherical and the second rod end of the first sliding rod may be hemispherical.

In some embodiments, the first shoe has a first side that faces the first sliding rod and a second side axially spaced apart from the first side. In some embodiments, the first side is formed to define a pocket sized to receive the second rod end of the first sliding rod, and the second side is coupled to a plurality of contact members arranged to contact a test article.

In some embodiments, the contact members may include a plurality of ball bearings that are partially received in the second side of the first shoe. In some embodiments, the plurality of ball bearings may include three ball bearings. Each ball bearing may have a center and the centers of the ball bearings may be arranged relative to one another to form an equilateral triangle. In some embodiments, the first sliding rod may extend along a first applicator axis and the first applicator axis may extend through a centroid of the equilateral triangle.

In some embodiments, the second load applicator includes a second sliding rod and a second shoe. The second sliding rod may extend axially between a first rod end and a second rod end of the second sliding rod. The first rod end of the second sliding rod may be arranged to engage the second end of the rocker arm. The second shoe may be arranged to engage the second rod end of the second sliding rod. In some embodiments, the first rod end of the second sliding rod may be hemispherical and the second rod end of the second sliding rod may be hemispherical.

In some embodiments, the second shoe may have a first side that faces the second sliding rod and a second side axially spaced apart from the first side. In some embodiments, the first side may be formed to define a pocket sized to receive the second rod end of the second sliding rod and the second side may be coupled to a plurality of contact members arranged to contact a test article.

In some embodiments, the contact members may include a plurality of ball bearings that are partially received in the second side of the second shoe. In some embodiments, the plurality of ball bearings may include three ball bearings, each ball bearing has a center, and the centers of the ball bearings arranged relative to one another to form an equilateral triangle. In some embodiments, the second sliding rod may extend along a second applicator axis and the second applicator axis extends through a centroid of the equilateral triangle.

According to another aspect of the present disclosure, a method of mechanically testing a test article may include a number of steps. The steps may include providing a load force along a load axis from a load rod to a rocker arm, pivoting the rocker arm about a rocker axis that is perpendicular to the load axis to cause the load force to be transferred to a first load applicator and a second load applicator spaced apart from the first load applicator, distributing the load force equally between the first load applicator and the second load applicator as an equally distributed load force, and applying the distributed load force to the test article.

In some embodiments, the step of applying the distributed load force to the test article may include articulating a first shoe about an end of the first load applicator to align the first shoe with the test article. In some embodiments, the first shoe may include a plurality of contact members that engage the test article and apply the distributed load force at a centroid to the plurality of contact members. In some embodiments, the plurality of contact members may include three ball bearings, each ball bearing has a center, and the centers of the ball bearings arranged relative to one another to form an equilateral triangle with the centroid at the center of the equilateral triangle.

In some embodiments, the step of applying the distributed load force to the test article may include articulating a second shoe about an end of the second load applicator to align the second shoe with the test article. In some embodiments, the second shoe may include a plurality of contact members that engage the test article and apply the distributed load force at a centroid to the plurality of contact members. In some embodiments, the plurality of contact members may include three ball bearings, each ball bearing has a center, and the centers of the ball bearings arranged relative to one another to form an equilateral triangle with the centroid at the center of the equilateral triangle.

According to another aspect of the present disclosure, a material testing system may include a load rod and a load distribution system. The load rod may be arranged to move axially along a load axis to provide a load force. The load distribution system may be coupled to the load rod for movement therewith. The load distribution system may include a first load applicator having a first sliding rod and a first shoe configured to articulate about an end of the first sliding rod and a second load applicator spaced apart from the first load applicator and having a second sliding rod and a second shoe configured to articulate about an end of the second sliding rod.

In some embodiments, the material testing system may further include a rocker arm coupled to the load rod for axial movement therewith. The rocker arm may be configured to pivot relative to the load rod about a rocker axis. The first and second sliding rods may be configured to translate axially relative to one another and engage the rocker arm to cause the rocker arm to pivot about the rocker axis and distribute the load force between the first and second sliding rods.

In some embodiments, the first shoe may include a first side formed to define a pocket sized to receive the end of the first sliding rod and a second side formed to receive a plurality of ball bearings that extend part way out of the second side. In some embodiments, the end of the first sliding rod may be hemispherical and the end of the second sliding rod may be hemispherical.

These and other features of the present disclosure will become more apparent from the following description of the illustrative embodiments.

DETAILED DESCRIPTION OF THE DRAWINGS

Figure 1:
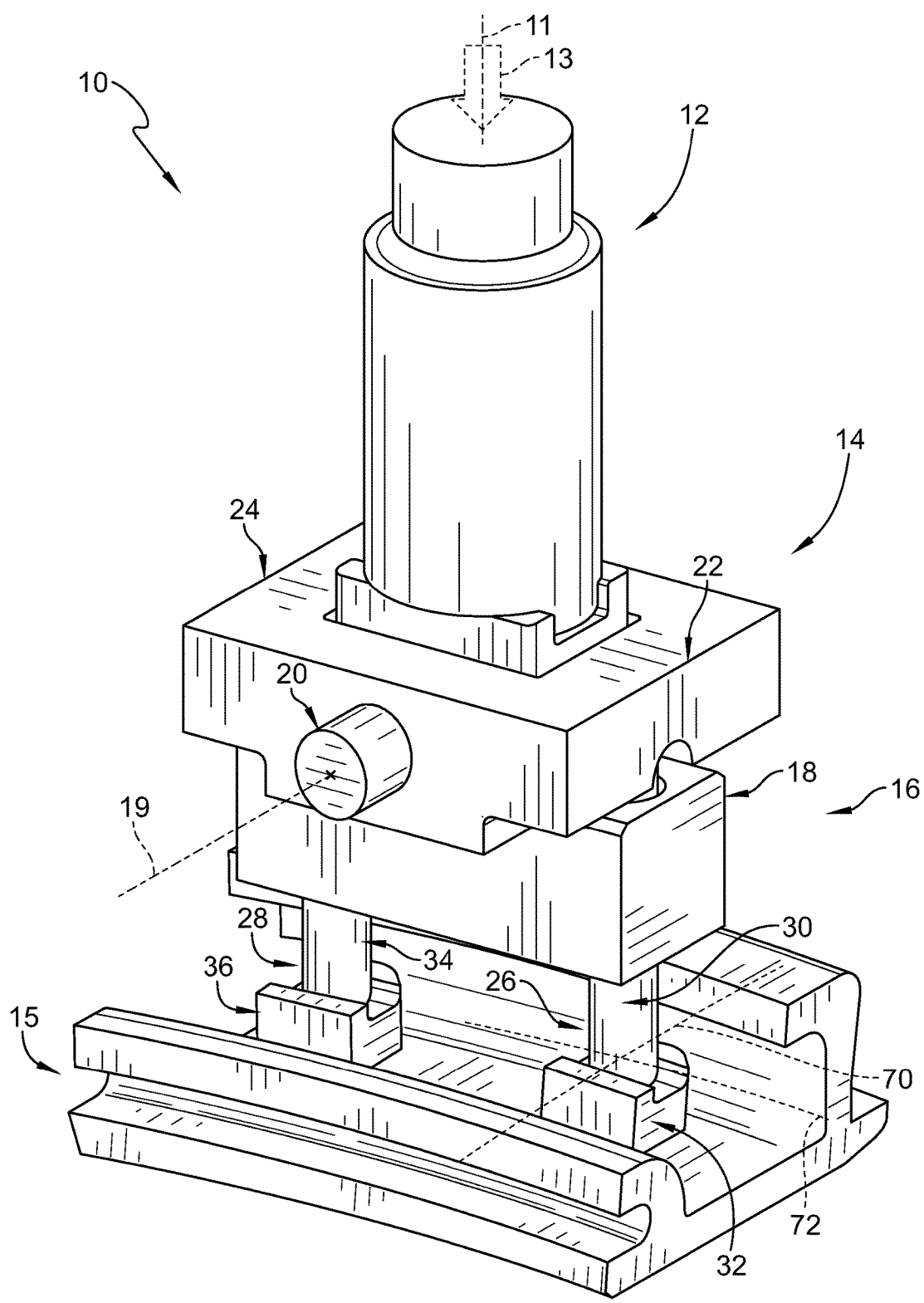
FIG. 1 is an enlarged perspective view of a material testing system and a test article to be tested by the material testing system.

For the purposes of promoting an understanding of the principles of the disclosure, reference will now be made to a number of illustrative embodiments illustrated in the drawings and specific language will be used to describe the same.

A material testing system 10 in accordance with the present disclosure includes a load rod 12, a rocker arm 14, and a load distribution system 16 as shown in FIG. 1. Load rod 12 is arranged to move along a load axis 11 to provide a load force 13 to a test article 15. Rocker arm 14 is coupled to load rod 12 for axial movement therewith. Load distribution system 16 is configured to engage rocker arm 14 to transfer load force 13 from load rod 12 and rocker arm 14 to test article 15.

Material testing system 10 can test a variety of testing articles 15 having different shapes and forms. Material testing system 10 uses load distribution system 16 to distribute load force 13 onto test article 15 while maintaining a predictable location of a resultant load of load force 13. Therefore, material testing system 10 is configured to adjust in response to portions of test article 15 having different heights by transferring load force 13 from load rod 12 to rocker arm 14 and then distributing load force 13 onto test article 15 with load distribution system 16.

Figure 2:
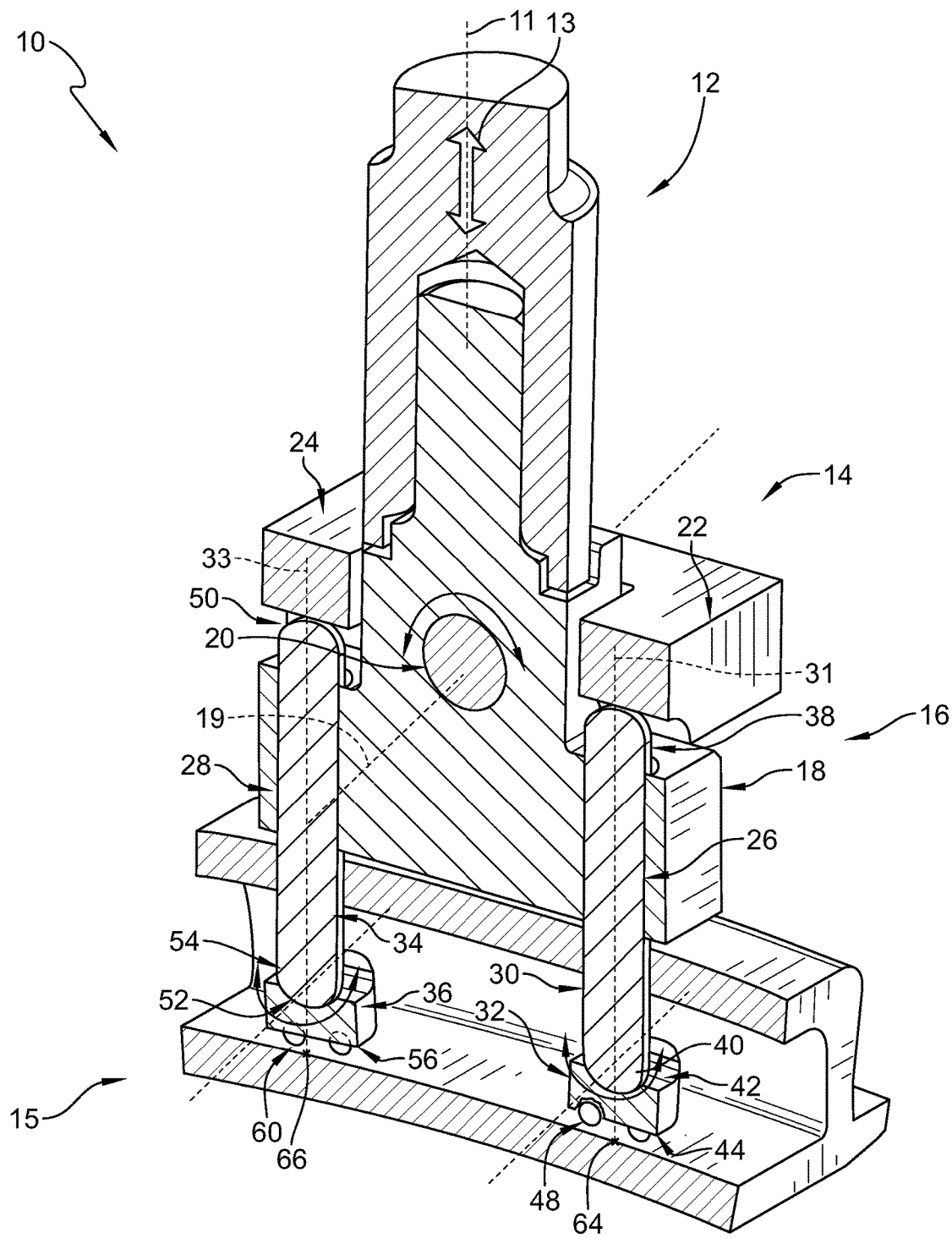
FIG. 2 is a sectional view of the material testing system of FIG. 1.

Load rod 12 includes a T-shaped body 18 and a pin 20 as shown in FIG. 2. T-shaped body 18 is configured to extend through rocker arm 14 so that rocker arm 14 is supported on load rod 12. Pin 20 extends through load rod 12 and rocker arm 14 along a rocker axis 19 and is configured to retain rocker arm 14 relative to load rod 12. Load force 13 is transferred from load rod 12 to rocker arm 14 when load rod 12 is coupled to rocker arm 14 by pin 20 as shown in FIG. 1.

Rocker arm 14 includes a first rocker end 22 and a second rocker end 24 as shown in FIGS. 1 and 2. First rocker end 22 is spaced apart from rocker axis 19 on one end of rocker arm 14. Second rocker end 24 is spaced apart from first rocker end 22 to locate rocker axis 19 between first rocker end 22 and second end 24 of rocker arm 14. Rocker arm 14 is configured to pivot relative to load rod 12 about rocker axis 19 when load force 13 is applied to test article 15 to tolerate portions of test article 15 having different heights and to allow load distribution system 16 to distribute load force 13 on test article 15.

Figure 3:
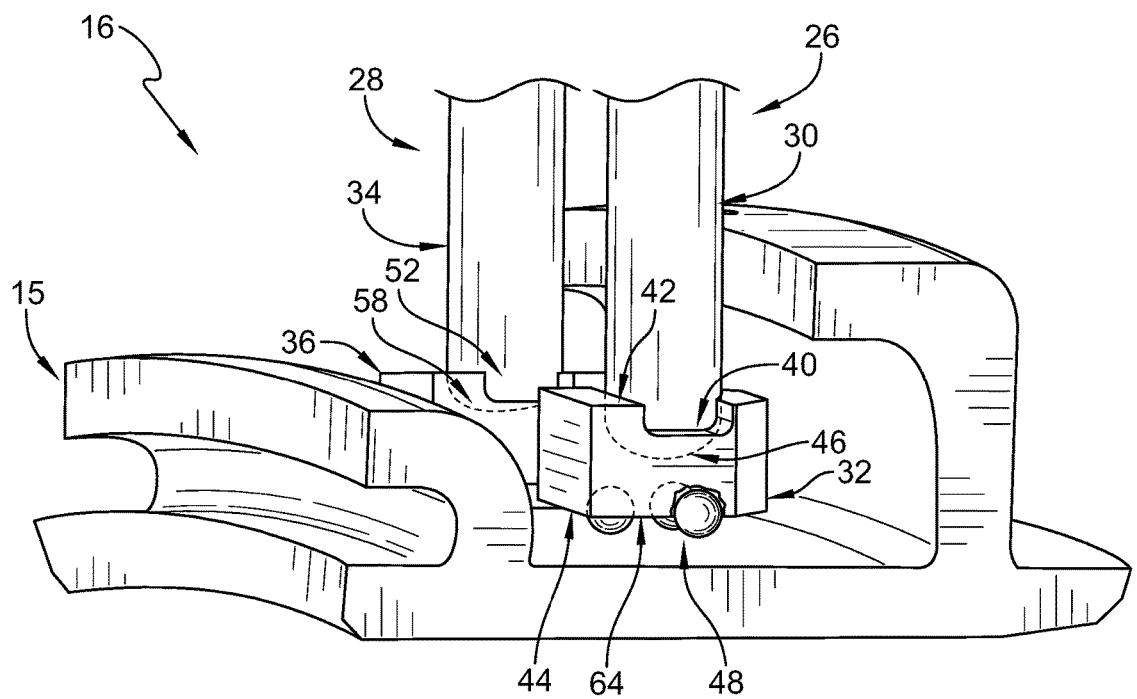
FIG. 3 is an enlarged perspective view of the material testing system of FIG. 1 showing that the material testing system includes first and second load applicators having first and second shoes for distributing the load from the material testing system to the test article.

Load distribution system 16 includes a first load applicator 26 and a second load applicator 28 as shown in FIGS. 1, 2, and 3. First load applicator 26 is arranged to engage first rocker end 22 of rocker arm 14. Second load applicator 28 is arranged to engage second rocker end 24 of rocker arm 14. First load applicator 26 and second load applicator 28 are configured to move axially relative to one another in response to engaging portions of test article 15 having different heights to cause rocker arm 14 to pivot about rocker axis 19 such that the rocker arm applies force load 13 equally between first load applicator 26 and second load applicator 28.

First load applicator 26 includes a first sliding rod 30 and a first shoe 32 as shown in FIGS. 1, 2, and 3. First sliding rod 30 is cylindrical and extends along a first load applicator axis 31 that is parallel to load axis 11 and extends through a center of first sliding rod 30. First sliding rod 30 is configured to slide along first load applicator axis 31 only. First shoe 32 is coupled to first sliding rod 30 and is configured to engage test article 15.

Second load applicator 28 includes a second sliding rod 34 and a second shoe 36 as shown in FIGS. 1, 2, and 3. Second sliding rod 34 is cylindrical and extends along a second load applicator axis 33 that is parallel to load axis 11 and first load applicator axis 31 and extends through a center of second sliding rod 34. Second sliding rod 34 is configured to slide along second load applicator axis 33 only. Second shoe 36 is coupled to first sliding rod 30 and is configured to engage test article 15.

First sliding rod 30 includes a first sliding rod end 38 and a second sliding rod end 40 as shown in FIG. 2. First sliding rod end 38 of first sliding rod 30 is arranged to extend through T-shaped body 18 of load rod 12 and engage first rocker end 22 of rocker arm 14. First sliding rod end 38 is configured to move with first rocker end 22 along first load applicator axis 31 relative to t-shaped body 18 as rocker arm 14 pivots in response to load distribution system 16 adjusting the distribution of load force 13 onto test article 15 due to portions of test article 15 having different heights. Second sliding rod end 40 is arranged to engage first shoe 32. First sliding rod end 38 and second sliding rod end 40 are hemispherical.

First shoe 32 includes a first shoe side 42 and a second shoe side 44 as shown in FIGS. 2 and 3. First shoe side 42 is axially spaced apart from second shoe side 44. First shoe side 42 is formed to define a first shoe pocket 46 that is sized to receive second sliding rod end 40 of first sliding rod 30. First shoe pocket 46 is hemispherical to allow movement of first shoe 32 about second sliding rod end 44. Second shoe side 44 is coupled to a plurality of contact members 48 that are arranged to engage test article 15. First shoe 32 is configured to articulate about second sliding rod end 40 so that second shoe side 44 and the plurality of contact members 48 are aligned with test article 15.

Second sliding rod 34 includes a first sliding rod end 50 and a second sliding rod end 52 as shown in FIG. 2. First sliding rod end 50 of second sliding rod 34 is arranged to extend through t-shaped body 18 of load rod 12 and engage second rocker end 24 of rocker arm 14. First sliding rod end 50 is configured to move with second rocker end 24 along second load applicator axis 33 relative to t-shaped body 18 as rocker arm 14 pivots in response to material testing system 10 adjusting the distribution of load force 13 due to portions of test article 15 having different heights. Second sliding rod end 52 is arranged to engage second shoe 36. First sliding rod end 50 and second sliding rod end 52 are hemispherical.

Second shoe 36 includes a first shoe side 54 and a second shoe side 56 as shown in FIGS. 2 and 3. First shoe side 54 is axially spaced apart from second shoe side 56. First shoe side 54 is formed to define a second shoe pocket 58 that is sized to receive second sliding rod end 52 of second sliding rod 34. Second shoe pocket 58 is hemispherical to allow movement of second shoe 36 about second sliding rod end 58. Second shoe side 56 is coupled to a plurality of contact members 60 that are arranged to engage test article 15. Second shoe 36 is configured to articulate about second sliding rod end 52 so that second shoe side 56 and the plurality of contact members 60 are aligned with test article 15.

Illustratively, first shoe 32 and second shoe 36 may articulate about second sliding rod ends 40, 52 along axes 70 and 72 as shown in FIG. 1. As such, first shoe 32 and second shoe 36 may articulate about second sliding ends 40, 52 freely along any axes and in any direction.

Figure 4:
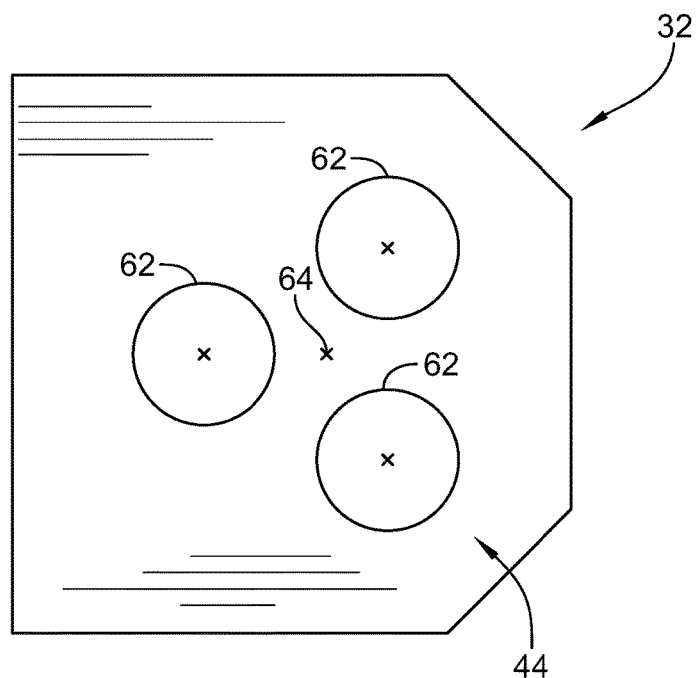
FIG. 4 is an enlarged perspective view of one of the shoes include in a load applicator of the material testing system of FIG. 3.

Contact members 48, 60 on first shoe 32 and second shoe 36 are a plurality of ball bearings that are partially received in second shoe sides 44, 56 as shown in FIGS. 2 and 3. The ball bearings are configured to allow movement of shoes 32, 36 across test article 15 as load distribution system 16 adjusts the distribution of load force 13 onto test article 15. Contact members 48 include three ball bearings 62 arranged relative to one another to form an equilateral triangle as shown in FIG. 4. Contact members 48 are the same as contact members 60 (not shown in FIG. 4) which are also arranged relative to one another to form an equilateral triangle. Each ball bearing 62 includes a center and the centers of the ball bearings are arranged relative to one another to form equilateral triangles with a centroid 64 formed by contact members 48 in first shoe 32 and centroid 66 formed by contract members 60 in second shoe 36.

In some embodiments, one ball bearing may be used to engage first and second shoes 32, 36 with test article 15. In another embodiment, two ball bearings may be used. In another embodiment, four ball bearings may be used. In some embodiments, any number of ball bearings may be used to distribute load force 13 onto test article 15 to maintain a predictable location of resultant load that is tolerant of relative displacements of first and second load applicators 26, 28 on test article 15.

Load rod 12 provides load force 13 along load axis 11 to rocker arm 14 via pin 20 as shown in FIG. 2. Load distribution system may encounter test article 15 having portions with different heights. The differences in heights across portions of test article 15 cause rocker arm 14 to pivot about rocker axis 19 and first and second load applicators 26, 28 to slide relative to load rod 12 and travel with rocker arm 14 along load applicator axes 31, 33, respectively. Simultaneously, first and second shoes 32, 36 articulate about first sliding rod ends 40, 52 of first and second load applicators 26, 28, respectively, to align first and second shoes 32, 36 with test article 15. After adjustment of load distribution system 16 is complete, load force 13 is then applied equally through contact members 48, 60. As such, load distribution system 16 applies load force 13 equally through first load applicator 26 and second load applicator 28 at the centroids 64, 66 of the equilateral triangles formed by ball bearings 62. This allows a predictable and repeatable center of loading from material testing system 10 to test article 15.

In some embodiments, when mechanically testing engineering articles comprised of high-hardness, high-stiffness materials, it may be desired to apply test loads in a uniform, repeatable, and predictable manner. This may be made more challenging by the surface texture of the test article. Due to these unique challenges for a select group of materials, ceramic matrix composite (CMC) materials may represent a challenging engineering problem. Testing for CMC articles may be helpful for characterizing the material, but mechanical testing of CMCs represents several obstacles to typical test methods. To address this problem, the enclosed mechanical testing concepts provides an approach to applying load to a CMC mechanical test article. Some embodiments illustrates a method for applying a distributed load to an irregular, high-hardness surface while maintaining a predictable location of resultant load that is tolerant of relative displacements of the load applicator and article surface.

In some embodiments, a load applicator component ends in a hemispherical feature that then seats into a hemispherical pocket of larger radius in a load shoe. The load shoe may house three contact features positioned such that the axis of the load applicator occurs at the centroid of an equilateral triangle formed by the three contact features. In some embodiments, the load application apparatus is configured to equally distribute the load from an applicator to an irregular surface while maintaining a predictable and repeatable center of loading. In some embodiments, should all three contact features of the load shoe encounter the surface of the test article at different heights, the load shoe may articulate about the end of the load applicator until equal force is applied at each of the three contact features.

In some embodiments, advantages of the approach described above include the ability to distribute load over an effective area and reducing the peak stresses associated with load application. In some embodiments, typical approaches to distributing loads involve the use of a larger load applicator, however, when applying load to an irregular, rigid surface, contact may only occur at discreet high points, concentrating loads at an unpredictable location(s) in the area of contact. In some embodiments, when utilizing the load application approach above to apply load to multiple locations which may receive equal loading, the mechanism illustrates an approach to overcome differential heights at each load application site.

Some embodiments show a mechanism that facilitates equal load application to two sites simultaneously, both of which utilize the previous concept to apply load to the surface of the test article. Some embodiments transmit load from a single source, through a pin, which is then distributed to the two load applicator rods.

In some embodiments, if the two load application sites occur at different heights relative to one another, the mismatch will cause the rocker arm to tilt and maintain contact with both rod ends. The rod ends may be free to slide within channels in the rocker arm and may be guided to only be capable of motion in the vertical direction. Thus, the apparatus may allow dissimilar load application heights while maintaining equal loading on both green load rods.

The enclosed mechanical testing concept suggests a solution to applying load to a CMC test article with irregular shapes. Some embodiments illustrate a method for applying a distributed load to an irregular, high-hardness surface while maintaining a predictable location of resultant load that is tolerant of relative displacements of the load applicator and article surface.

While the disclosure has been illustrated and described in detail in the foregoing drawings and description, the same is to be considered as exemplary and not restrictive in character, it being understood that only illustrative embodiments thereof have been shown and described and that all changes and modifications that come within the spirit of the disclosure are desired to be protected.

What is claimed is:

1. A material testing system for loading test articles, the material testing system comprising
    a load rod arranged to move along a load axis to provide a load force to a test article,
    a rocker arm coupled to the load rod for axial movement therewith, the rocker arm including a rocker axis that intersects the load axis, a first end spaced apart from the rocker axis, and a second end spaced apart from the first end to locate the rocker axis between the first end and the second end of the rocker arm, and the rocker arm configured to pivot relative to the load rod about the rocker axis, and
    a load distribution system configured to engage the rocker arm to transfer the load force from the load rod and rocker arm to the test article, the load distribution system including a first load applicator configured to engage the first end of the rocker arm and a second load applicator configured to engage the second end of the rocker arm, the first load applicator and the second load applicator configured to move axially relative to one another and relative to the load axis in response to engaging portions of the test article having different heights to cause the rocker arm to pivot about the rocker axis such that the rocker arm applies the force load equally between the first load applicator and the second load applicator,
    wherein the first load applicator and the second load applicator are blocked from moving radially relative to the load axis.

2. The material testing system of claim 1, wherein the first load applicator includes a first sliding rod and a first shoe, the first sliding rod extends axially between a first rod end and a second rod end of the first sliding rod, the first rod end of the first sliding rod is arranged to engage the first end of the rocker arm, and the first shoe is arranged to engage the second end of the first sliding rod.

3. The material testing system of claim 2, wherein the first rod end of the first sliding rod is hemispherical and the second rod end of the first sliding rod is hemispherical.

4. The material testing system of claim 2, wherein the first shoe has a first side that faces the first sliding rod and a second side axially spaced apart from the first side, the first side is formed to define a pocket sized to receive the second rod end of the first sliding rod, and the second side is coupled to a plurality of contact members arranged to contact a test article.

5. The material testing system of claim 4, wherein the contact members include a plurality of ball bearings that are partially received in the second side of the first shoe.

6. The material testing system of claim 5, wherein the plurality of ball bearings include three ball bearings, each ball bearing has a center, and the centers of the ball bearings are arranged relative to one another to form an equilateral triangle.

7. The material testing system of claim 6, wherein the first sliding rod extends along a first applicator axis and the first applicator axis extends through a centroid of the equilateral triangle.

8. The material testing system of claim 2, wherein the second load applicator includes a second sliding rod and a second shoe, the second sliding rod extends axially between a first rod end and a second rod end of the second sliding rod, the first rod end of the second sliding rod is arranged to engage the second end of the rocker arm, and the second shoe is arranged to engage the second rod end of the second sliding rod.

9. The material testing system of claim 8, wherein the first rod end of the second sliding rod is hemispherical and the second rod end of the second sliding rod is hemispherical.

10. A material testing system comprising
    a load rod arranged to move axially along a load axis to provide a load force,
    a load distribution system coupled to the load rod for movement therewith, the load distribution system including a first load applicator having a first sliding rod and a first shoe configured to articulate about an end of the first sliding rod and a second load applicator spaced apart from the first load applicator and having a second sliding rod and a second shoe configured to articulate about an end of the second sliding rod, and
    a rocker arm coupled to the load rod for axial movement therewith, the rocker arm configured to pivot relative to the load rod about a rocker axis, and the first and second sliding rods are configured to translate axially relative to one another and engage the rocker arm to cause the rocker arm to pivot about the rocker axis and distribute the load force between the first and second sliding rods,
    wherein the first shoe includes a first side formed to define a pocket sized to receive the end of the first sliding rod and a second side formed to receive a plurality of ball bearings that extend part way out of the second side.

11. The material testing system of claim 10, wherein the end of the first sliding rod is hemispherical and the end of the second sliding rod is hemispherical.

12. A method of mechanically testing a test article, the method comprising
    providing a load force along a load axis from a load rod to a rocker arm, pivoting the rocker arm about a rocker axis that is perpendicular to the load axis to cause the load force to be transferred to a first load applicator and a second load applicator spaced apart from the first load applicator, distributing the load force equally between the first load applicator and the second load applicator as an equally distributed load force, and applying the distributed load force to the test article, wherein the first load applicator and the second load applicator are configured to move axially relative to one another and relative to the load axis in response to engaging portions of the test article having different heights and the first load applicator and the second load applicator are blocked from moving radially relative to the load axis.

13. The method of claim 12, wherein the step of applying the distributed load force to the test article includes articulating a first shoe about an end of the first load applicator to align the first shoe with the test article.

14. The method of claim 13, wherein the first shoe includes a plurality of contact members that engage the test article.

15. The method of claim 14, wherein the plurality of contact members include three ball bearings, each ball bearing has a center, and the centers of the ball bearings are arranged relative to one another to form an equilateral triangle with a centroid at the center of the equilateral triangle.

16. The method of claim 13, wherein the step of applying the distributed load force to the test article includes articulating a second shoe about an end of the second load applicator to align the second shoe with the test article.

17. The method of claim 16, wherein the second shoe includes a plurality of contact members that engage the test article.

18. The method of claim 17, wherein the plurality of contact members include three ball bearings, each ball bearing has a center, and the centers of the ball bearings arranged relative to one another to form an equilateral triangle with a centroid at the center of the equilateral triangle.

* * * * *